United States Patent [19]

Kontos et al.

[11] Patent Number: 5,404,888
[45] Date of Patent: Apr. 11, 1995

[54] GUIDE WIRE EXTENSION

[75] Inventors: Stavros B. Kontos, Woodcliff Lake; Kenneth F. Kaltenbach, Leonia; Irwin S. Wolosky, Parsippany, all of N.J.

[73] Assignee: Datascope Investment Corp., Montvale, N.J.

[21] Appl. No.: 179,872

[22] Filed: Jan. 11, 1994

Related U.S. Application Data

[63] Continuation of Ser. No. 833,035, Feb. 10, 1992, abandoned.

[51] Int. Cl.⁶ ............................................. A61B 5/00
[52] U.S. Cl. ................................. 128/772; 604/283
[58] Field of Search ............... 128/657, 772; 604/95, 604/164, 280–284

[56] References Cited

U.S. PATENT DOCUMENTS

| | | | |
|---|---|---|---|
| 4,655,762 | 4/1987 | Rogers | 604/283 |
| 4,827,941 | 5/1989 | Taylor et al. | 128/772 |
| 4,834,719 | 5/1989 | Arenas | 604/283 |
| 4,850,984 | 7/1989 | Harris | 604/283 |
| 4,875,489 | 10/1989 | Messner | 128/772 |
| 4,917,103 | 4/1990 | Gambale et al. | 128/772 |
| 4,922,923 | 5/1990 | Gambale et al. | 128/772 |
| 4,966,163 | 10/1990 | Kraus et al. | 128/772 |
| 5,031,636 | 7/1991 | Gambale et al. | 128/772 |
| 5,109,867 | 5/1992 | Twyford | 128/772 |
| 5,117,838 | 6/1992 | Palmer et al. | 128/657 |
| 5,188,621 | 2/1993 | Samson | 128/657 |
| 5,197,486 | 3/1993 | Frassica | 128/657 |

*Primary Examiner*—Max Hindenburg
*Attorney, Agent, or Firm*—Fish & Richardson

[57] ABSTRACT

Guide wire extension connecting means are described in which a stretchable tube acts as the connecting element. The stretchable tube has a lumen or recess into which the guide wire is inserted. As withdrawal of the guide wire is attempted, the connecting element stretches and collapses, thereby grabbing the guide wire and resisting withdrawal.

23 Claims, 1 Drawing Sheet

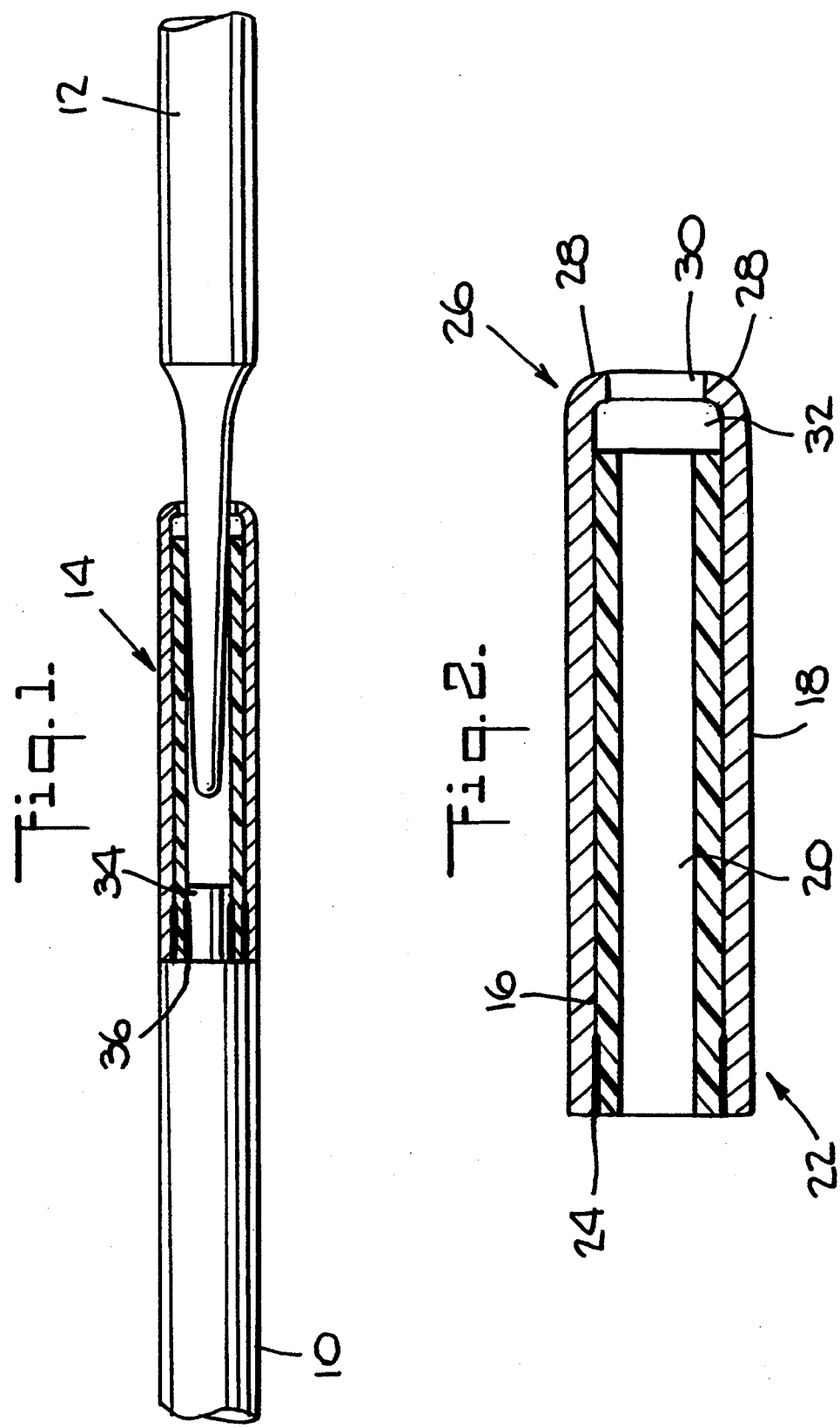

GUIDE WIRE EXTENSION

This is a continuation of application Ser. No. 07/833,035, filed Feb. 10, 1992, now abandoned.

BACKGROUND OF THE INVENTION

This invention relates to means for joining together two tubular bodies, primarily those used during percutaneous transluminal coronary angioplasty (PTCA). More particularly, this invention relates to means for joining an extension wire to a guide wire to facilitating catheter exchanges during angioplasty.

Those skilled in the art of PTCA know that it is frequently necessary, during an angioplasty procedure, to exchange balloon catheters. Most commonly this is done to exchange a catheter having a balloon of one size for one having a balloon of a different size.

Normally, PTCA catheters are inserted over guide wires. The guide wire may be inserted first, followed by the catheter, or alternatively, the two may be assembled outside the body and then inserted as a unit. The guide wire is typically between about 20 and 50 cm. longer than the catheter. The guide wire, either as part of the assembled unit, or separately, is fed up through the arterial tree until its distal tip has passed through the stenosis to be opened. Generally, the distal tip of the guide wire is provided with a radiopaque marker so that the physician can determine, using fluoroscopy, its location within the body. Once the guide wire is in place, the PTCA catheter is advanced until its balloon is within the stenosis. Typically, the PTCA catheter is also provided with radiopaque markers at its distal end so that the location of the balloon can be confirmed under fluoroscopy.

Often the first PTCA catheter must be removed and replaced with another. The need for an exchange may arise because the first balloon selected is too large to enter the stenosis and a second, smaller balloon must be substituted for it. The need for the exchange may also arise because the first balloon, while small enough to enter the stenosis, is not large enough to open the lumen sufficiently to provide adequate perfusion. A second, larger balloon must then be substituted for the first to open the lumen further.

Once the physician has been successful in having the guide wire negotiate the often tortuous path to the lesion, it is important that the path to the lesion be maintained during balloon exchange. One way this has been accomplished in the past is by replacing the guide wire with a much longer exchange wire. To do this, the guide wire is first removed, leaving the catheter in place. The guide wire is then replaced with a much longer exchange wire. During this procedure, the first catheter remains in place, providing a channel for the exchange wire to follow to the lesion, hence the exchange wire need not negotiate the path anew. The first catheter can then be removed and the second one inserted over the exchange wire without ever losing control over the wire.

Once the exchange has been made, however, it is generally considered highly desireable not to have the long proximal end of the exchange wire extend from the catheter. It is very unwieldy, it gets in the way during the subsequent angioplasty procedure, it can fall and drag on the floor, getting dirty and contaminated and is generally at the very least a nuisance. Therefore, another exchange is often performed, this one to replace the exchange wire with a much shorter guide wire.

Another method that has been used to substitute one catheter for another without losing control over the wire involves attaching a guide wire extension to the proximal end of the guide wire. One means of attaching such an extension wire is shown in U.S. Pat. No. 4,917,103 in which the two wires are attached by means of a crimping action. Although this method provides for a reasonably secure junction, it makes it very difficult to detach the two wires when the exchange has been completed.

A second means for attaching the extension wire to the guide wire, as described in U.S. Pat. No. 4,827,941, involves the use of a tubular connector. This connector is fixedly attached, at one end, to the extension wire, and is adapted to receive the guide wire into its other end. The diameter of the guide wire opening in the connector of the '941 patent is larger that the portion of the guide wire to be inserted therein. The guide wire, therefore, is provided with an undulating proximal end, the diameter of which, as measured from upper peak to lower peak, being greater than the inside diameter of the connector. Because of these undulations, when the guide wire is inserted into the connector, a friction fit is assured, with contact being made between the peaks of the undulations and the inside wall of the connector.

SUMMARY OF THE INVENTION

The instant invention provides a new and improved device for attaching an extension wire to a guide wire in such fashion that the junction is sufficiently secure to prevent inadvertent separation but which permits the two wires to be disconnected when balloon exchange has been completed.

Connection of the extension wire to the guide wire, according to the instant invention, is accomplished through the use of a stretchable, deformable, preferably plastic, short connector. The connector is preferably a hollow tube with a lumen running from end to end. Into one end is inserted the guide wire, and into the other end is inserted the extension wire. Because the connector is stretchable, when opposite axial forces are exerted on the two wires, the connector tends to stretch and as it stretches its diameter tends to decrease, thereby grabbing the wires inside. The greater the force exerted to separate the wires, the greater tends to be the grabbing force of the connector.

Since it is desired that the wires be disconnected after the balloon exchange has been completed, means are provided for limiting the amount of axial stretch of the connector, thereby assuring that the connector will exert only a predetermined grabbing force. In the preferred embodiment, this is accomplished by placing a jacket over the stretchable plastic tube and providing the jacket with a flange at the end. Since there is a gap between the end of the plastic tube and the flange, the plastic tube is permitted to stretch somewhat, but only until it abuts the flange.

BRIEF DESCRIPTION OF THE DRAWINGS

FIG. 1 is a plan view, partially in section, of an extension wire attached, through the use of a connector, to a guide wire in accordance with the invention.

FIG. 2 is a sectional view of a connector according to the preferred embodiment of the invention.

DETAILED DESCRIPTION OF THE INVENTION

As best seen in FIG. 1, extension wire 10 and guide wire 12 are joined together through the use of connector 14. Connector 14 is comprised of stretchable tube 16 and jacket 18. Connector tube 16 is provided with lumen 20 running therethrough from proximal end 22 to distal end 26. Overlying distal end 26 of connector tube is jacket 18. Connector tube 16 and jacket 18 may be joined together, as for example, by the use of adhesive 24. The distal end of jacket 18 is bent inwardly to form a flange 28, leaving an opening 30 therethrough of about the same diameter as the diameter of lumen 20. The distal end 26 of connector tube 16 does not reach all the way to flange 28, leaving a gap 32.

Extension wire 10 is preferably TEFLON ®-coated stainless steel having a diameter of about 0.014 inches and a length of about 57 inches. Its distal tip 34 is about 0.2 inches long and is ground to a diameter of about 0.006 inches to permit insertion into lumen 20. Tip 34 is inserted into lumen 20 from the proximal end 22 and may be affixed therein, for example, by the use of adhesive 36. The adhesive can also be used to form a bond between the proximal end 22 of jacket 18 and extension wire 10.

Guide wire 12 is preferably also TEFLON ®-coated stainless steel having a diameter of about 0.014 inches and a length of about 175 cm. Its proximal end 38 is about 0.8 inches long and is ground down to a slight taper having a tip diameter of about 0.006 inches and a taper angle of about ¼°. This configuration permits insertion through opening 30 and into the distal end of lumen 20.

The connector tube 16 is preferably about 1.475 inches in length with the lumen 20 having a diameter of about 0.007 inches. Jacket 18 is about 1.5 inches in length after the forming of flange 28. Gap 32 is preferably on the order of about 0.025 inches. It will be understood, however, that none of the dimensions set forth herein is critical. They are being provided merely as being exemplary.

Connector tube 16 may be made of any stretchable material, for example, deformable plastic or rubber. Preferably it is a polyimide. It also may be formed of a non-stretchable material that has been fabricated so as to be stretchable. For example, it may be made of stainless steel wire that has been woven into the form of a tubular braid. Although the steel wires in such a structure do not themselves stretch, the braid into which they are woven can stretch considerably.

Jacket 18 may be made of any material which is substantially non-stretchable, such as stainless steel. The selection of the adhesive or other affixing medium is determined by the nature of the materials selected for the other components. When the stretch tube 16 is a polyimide, the jacket is stainless steel and the extension wire is stainless steel, it has been found that a cyanoacrylate adhesive works quite well.

In the preferred method of practicing the invention, the extension wire is supplied with connector 14 permanently affixed thereto. It is attached to the guide wire by sliding the open end of the connector over the proximal end of the guide wire until the tapered tip is seated in lumen 20. While a special tool may be employed to facilitate this insertion, use thereof is not essential. Security of the connection can then be tested by grasping the guide wire in one hand and the extension wire in the other and pulling gently in opposite directions.

Once the guide wire is properly seated inside lumen 20, any attempt to pull the guide wire out will be met with far more resistance than was encountered during the insertion process. This is because the pulling action causes tube 16 to stretch in the axial direction, which stretching tends to cause lumen 20 to collapse. As the lumen collapses, tube 16 grabs the end of the guide wire within, thereby resisting withdrawal of the guide wire. The greater the stretching, the stronger the grabbing force.

In order that the grabbing force not be so great as to prevent the physician from disconnecting the extension wire after the balloon exchange has been completed, jacket 18 is provided. As the guide wire is pulled from the connector, tube 16 begins to stretch, thereby resisting removal and preventing inadvertent separation. The amount of stretch, however is limited by flange 28 of jacket 18. Once tube 16 has stretched far enough so that it has closed gap 32, further stretching is prevented by flange 28. Thus, the amount of force necessary to separate the extension wire from the guide wire is a function of the size of gap 32, and the size of that gap can be selected to permit separation only upon application of a predetermined amount of force. With the dimensions set forth above, a gap of about 0.025 inches permits the extension wire to be disconnected when a force of about 0.4 pounds is exerted.

Although connector 14 has been depicted with a lumen running from end to end, that is not necessary. A portion of the stretch tube may be solid rather than hollow. Also, the connector need not be permanently attached to the extension wire. It can, for example, be attached to the guide wire or it need not be permanently attached to either wire. Proximal end 22 of connector 14 may be formed to be a mirror image of distal end 26 thereby leaving a gap at each end. With that structure, tube 16 could stretch at both ends until both distal and proximal gaps are closed. As yet another alternative, proximal end 22 may be formed as a mirror image of distal end 26, but without a gap, in which case stretching would occur at only one end.

Other changes, modifications and alternative structures will readily occur those skilled in the art, and all such obvious variations fall within the scope of the broad invention as described herein and as defined in the claims set forth below.

What is claimed is:

1. A connector for connecting a medical guidewire of limited dimension sized to access remote regions of the body to an extension wire of substantially corresponding size, the medical guidewire having a reduced diameter proximal end with an outer diameter that is smaller than the outer diameter of the main body of said guidewire, said connector comprising:

a non-stretchable limited dimension outer tube having proximal and distal ends, an outer diameter generally corresponding to that of the main body of the guidewire, and an inner wall surface, the proximal end of said outer tube being adapted to couple to the distal end of the extension wire; and an inner tube having a hollow distal end of deformable plastic or elastomeric material disposed within and with its outer surface in constrained contact with the inner wall surface of said outer tube, said deformable plastic or elastomeric inner tube having an inner wall surface of inner diameter less than the outer diameter of at least a portion of the reduced diameter proximal end of said guidewire for detachably gripping the outer surface of the proximal end of the guidewire, wherein, as a result of deformation of the thickness of said inner tube against the constraint provided by said outer tube, the inner wall surface of said inner tube provides resistance to removal of the proximal end of the guidewire for resisting the separation of the guidewire from said extension wire.

2. The connector of claim 1 wherein said inner tube has an outer surface fixedly attached to the inner wall surface of said outer tube.

3. The connector of claim 1 wherein said inner tube extends between the proximal and distal ends of said outer tube.

4. The connector of claim 1 wherein the proximal end of said outer tube is fixedly attached to the distal end of the extension wire.

5. The connector of claim 1 wherein the outer diameter of said outer tube is on the order of 0.014 inches and the inner diameter of said outer tube is on the order of 0.007 inches.

6. The connector of claim 1 wherein said inner tube is made of rubber.

7. The connector of claim 1 wherein said inner tube is made of polyimid.

8. The connector of claim 1 wherein said outer tube is made of stainless steel.

9. The connector of claim 1 wherein said inner tube is made of rubber and said outer tube is made of stainless steel.

10. The connector of claim 1 wherein said outer tube comprises a flange at its distal end forming a gap between an inner surface of said flange and the distal end of said inner tube for limiting the amount of axial stretch of said inner tube.

11. The connector of claim 10 wherein said gap is on the order of 0.025 inches in length.

12. The connector of claim 1 wherein said inner tube has a hollow proximal end for detachably gripping the distal end of the extension wire.

13. The connector of claim 12 wherein said outer tube comprises flanges located at the distal and proximal ends of said outer tube for respectively limiting the amount of axial stretch of said inner tube in distal and proximal directions.

14. A guidewire exchange system comprising:
a medical guidewire of limited dimension sized to access remote regions of the body, the medical guidewire having a reduced diameter proximal end with an outer diameter that is smaller than the outer diameter of the main body of said guidewire;
an extension wire having an outer diameter substantially corresponding to the outer diameter of said guidewire; and
a connector for connecting said guidewire said extension wire comprising: a non-stretchable limited dimension outer tube having proximal and distal ends, an outer diameter generally corresponding to that of the main body of the guidewire, and an inner wall surface, the proximal end of said outer tube being adapted to couple to the distal end of the extension wire; and an inner tube having a hollow distal end of deformable plastic or elastomeric material disposed within and with its outer surface in constrained contact with the inner wall surface of said outer tube, said deformable plastic or elastomeric inner tube having an inner wall surface of inner diameter less than the outer diameter of at least a portion of said reduced diameter proximal end of said guidewire for detachably gripping the outer surface of the proximal end of the guidewire, wherein, as a result of deformation of the thickness of said inner tube against the constraint provided by said outer tube, the inner wall surface of said inner tube provides resistance to removal of the proximal end of the guidewire for resisting the separation of the guidewire from said extension wire.

15. The system of claim 14 wherein said inner tube has an outer surface fixedly attached to the inner wall surface of said outer tube.

16. The connector of claim 14 wherein said inner tube extends between the proximal and distal ends of said outer tube.

17. The connector of claim 14 wherein the proximal end of said outer tube is fixedly attached to the distal end of the extension wire.

18. The connector of claim 14 wherein the inner wall surface of said inner tube is made of rubber and said outer tube is made of stainless steel.

19. A connector for connecting a medical guidewire of limited dimension sized to access remote regions of the body to an extension wire of substantially corresponding size, the medical guidewire having a reduced diameter proximal end with an outer diameter that is smaller than the outer diameter of the main body of the guidewire, said connector comprising:
constraining means having proximal and distal ends, an outer diameter generally corresponding to that of the main body of the guidewire, and an inner wall surface, the proximal end of said constraining means including means for coupling to the distal end of the extension wire; and
gripping means of deformable plastic or elastomeric material disposed within and with its outer surface in constrained contact with said constraining means, said deformable plastic or elastomeric gripping means having an inner wall surface of inner diameter less than the outer diameter of at least a portion of said reduced diameter proximal end of said guidewire for detachably gripping the outer surface of the proximal end of the guidewire, wherein, as a result of deformation of the thickness of said gripping means against the constraint provided by said constraining means, the inner wall surface of said gripping means provides resistance to removal of the proximal end of the guidewire for resisting the separation of the guidewire from said extension wire.

20. The connector of claim 19 wherein said gripping means is fixedly attached to said constraining means.

21. The connector of claim 19 wherein said gripping means extends between the proximal and distal ends of said constraining means.

22. The connector of claim 19 wherein said constraining means is fixedly attached to the distal end of the extension wire.

23. The connector of claim 19 wherein said gripping means is made of rubber.

* * * * *

UNITED STATES PATENT AND TRADEMARK OFFICE
CERTIFICATE OF CORRECTION

PATENT NO.   : 5,404,888

DATED        : April 11, 1995

INVENTOR(S)  : Stavros B. Kontos et al.

It is certified that error appears in the above-identified patent and that said Letters Patent is hereby corrected as shown below:

Cover sheet, under [56] References Cited, U.S. PATENT DOCUMENTS, please insert the following:

```
5,113,872   5/1992    Jahrmarkt et al. ...... 128/772
5,191,888   3/1993    Palmer et al. ......... 128/657
RE34466     12/1993   Taylor et al. ......... 128/657
5,271,415   12/1993   Foerster et al. ....... 128/772
```

Signed and Sealed this

Fourteenth Day of May, 1996

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO.  : 5,404,888

DATED       : April 11, 1995

INVENTOR(S) : Stavros B. Kontos et al.

It is certified that error appears in the above-identified patent and that said Letters Patent is hereby corrected as shown below:

On the title page, item [73], change assignee to:

Boston Scientific Corporation
a Delaware Corporation
One Boston Scientific Place
Natick, MA 01760-1537

Signed and Sealed this

Fifth Day of November, 1996

Attest:

BRUCE LEHMAN

Attesting Officer    Commissioner of Patents and Trademarks